United States Patent [19]

Cartwright et al.

[11] 4,414,391

[45] Nov. 8, 1983

[54] A PROCESS FOR PREPARING 2-PYRIDINYLOXYPHENOXY-LOWER-ALKANOATES

[75] Inventors: David Cartwright, Woodley; Michael Turnbull, Lower Earley, both of England

[73] Assignee: Imperial Chemical Industries PLC, London, England

[21] Appl. No.: 259,926

[22] Filed: May 4, 1981

[30] Foreign Application Priority Data

May 15, 1980 [GB] United Kingdom ................. 8016028

[51] Int. Cl.$^3$ ........................................... C07D 213/64
[52] U.S. Cl. .................................. 546/302; 546/291; 546/300; 71/94
[58] Field of Search ......................... 546/302, 300, 291

[56] References Cited

FOREIGN PATENT DOCUMENTS

| 1473 | 4/1979 | European Pat. Off. ............ 546/302 |
| 24907 | 3/1981 | European Pat. Off. ............ 546/302 |
| 2905458 | 10/1978 | Fed. Rep. of Germany ...... 546/302 |
| 2921567 | 1/1980 | Fed. Rep. of Germany ...... 546/302 |
| 2016464A | 10/1978 | United Kingdom ................ 546/302 |
| 2020651A | 11/1979 | United Kingdom .................... 71/94 |
| 2025400A | 1/1980 | United Kingdom ................ 546/302 |

*Primary Examiner*—Alan L. Rotman
*Attorney, Agent, or Firm*—Cushman, Darby & Cushman

[57] ABSTRACT

This invention relates to a process for preparing pyridyloxyphenoxypropanecarboxylic acids and their derivatives, and to intermediates useful in the process.

1 Claim, No Drawings

A PROCESS FOR PREPARING 2-PYRIDINYLOXYPHENOXY-LOWER-ALKANOATES

BACKGROUND OF THE INVENTION

Our European Patent Application No. 78300203.3 (Publication No. 0001473; the disclosure of this Application is incorporated herein by reference) discloses inter alia compounds of general formula (I):

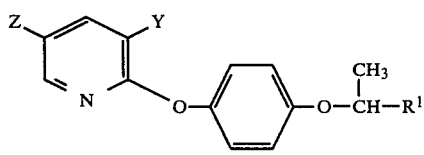

wherein each of Z and Y, which may be the same or different, is hydrogen, fluorine, chlorine, bromine, iodine, trifluoromethyl, difluoromethyl or chlorodifluoromethyl, provided at least one of Z and Y is trifluoromethyl, difluoromethyl or chlorodifluoromethyl; and $R^1$ is cyano; carboxy; a group of general formula —$CONR^2R^3$ wherein $R^2$ is hydrogen or alkyl and $R^3$ is hydrogen, $C_{1-4}$ alkoxy, optionally hydroxy- or phenyl-substituted $C_{1-4}$ alkyl, optionally halo-substituted phenyl, a group of general formula —$NR^4R^5$ wherein $R^4$ is hydrogen or $C_{1-4}$ alkyl and $R^5$ is hydrogen, $C_{1-4}$ alkyl or optionally halo-substituted phenyl, or $R^2$ and $R^3$ form together with the nitrogen to which they are attached pyrrolidino, piperidino or morpholino; a group of general formula —$COSR^6$ wherein $R^6$ is alkyl or phenyl; optionally halo-, alkoxy- or hydroxy-substituted alkoxycarbonyl; a group of general formula:

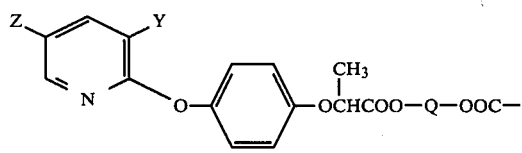

wherein Z and Y are as defined above and Q is alkylene; a group of general formula —$CO(OCH_2CH_2)_nOR^7$ wherein $R^7$ is $C_{1-4}$ alkyl and n is an integer of 1 to 5; optionally halo- or methyl-substituted cyclohexyloxycarbonyl; ($C_{3-6}$ alkenyl) oxycarbonyl; optionally halo- or methyl-substituted phenoxycarbonyl; or benzyloxycarbonyl, the phenyl moiety of which being optionally ring-substituted with halogen or methyl; and, in the case of compounds wherein $R^1$ is carboxyl, the salts of said compounds. The compounds have selective herbicidal activity.

The above compounds can be prepared, and this forms part of the present invention, by reducing a compound of general formula (II):

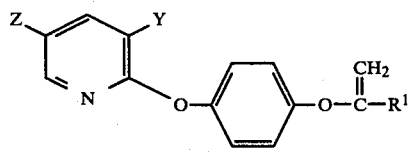

wherein Z, Y and $R^1$ are as defined above, and if necessary, when $R^1$ in the compound of general formula (I) so obtained is not the desired group, converting it in known manner to give a compound of general formula (I) where $R^1$ is the desired group.

The compounds of general formula (II) can be prepared (a) by reacting a compound of general formula (III):

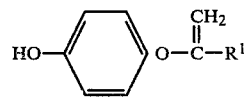

wherein $R^1$ is as defined above, or a salt (for example an alkali metal, e.g. sodium or potassium salt) thereof, with a compound of general formula (IV):

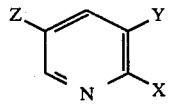

wherein Z and Y are as defined above and X is halogen (e.g. fluorine, chlorine or bromine); or (b) by reacting a compound of general formula (V):

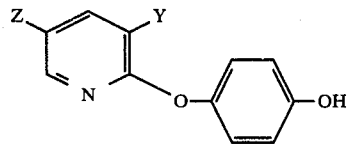

where Z and Y are as defined above, or a salt thereof, with a compound of general formula (VI):

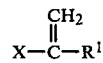

wherein $R^1$ and X are as defined above; and, when $R^1$ in the compound of general formula (II) obtained in (a) or (b) is not the desired group, converting it in known manner to give a compound of general formula (II) where $R^1$ is the desired group.

The compounds of general formula (III) can be prepared by reacting hydroquinone or a salt thereof (for example a di-alkali metal salt e.g. a di-sodium or potassium salt) with a compound of general formula (VI) wherein $R^1$ and X are as defined above, and when $R^1$ in the compound of general formula (III) so obtained is not the desired group, converting it in known manner to give a compound of general formula (III) where $R^1$ is the desired group.

The process can be illustrated by the reaction sequences given below for the preparation of the compound of general formula (I) wherein Z is trifluoromethyl, Y is hydrogen and $R^1$ is n-butyl:

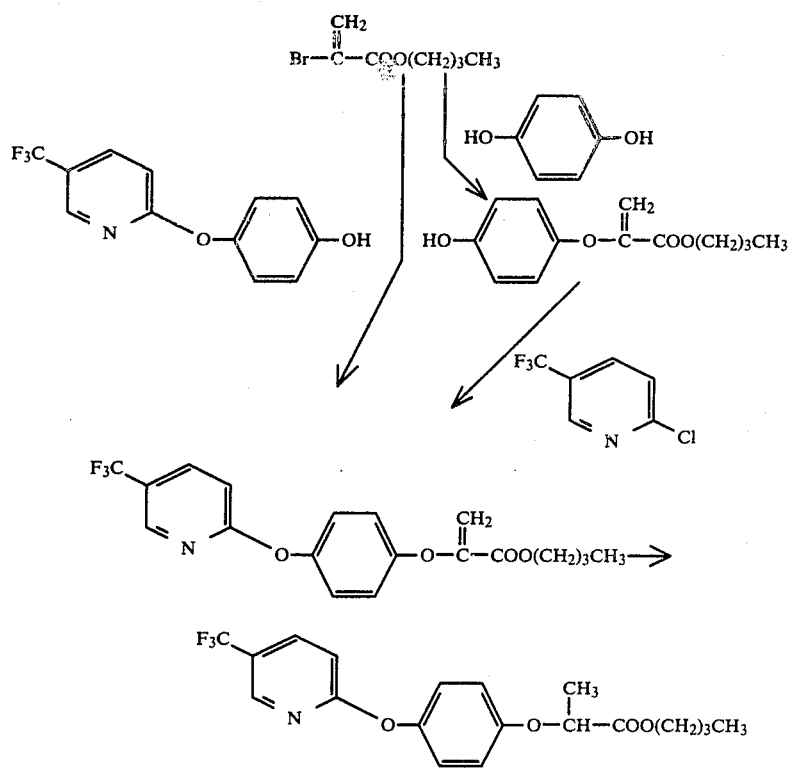

The preparation of the compound of general formula (II) by reacting the compound of general formula (V) and the compound of general formula (VI) and the preparation of the compound of general formula (III) by reacting hydroquinone or a salt thereof with a compound of general formula (VI) can be performed by reacting (e.g. by heating) the ingredients in a polar solvent (for example acetone) in the presence of a dry base for example an alkali metal carbonate (e.g. sodium or potassium carbonate). Preferably, in the latter reaction, only one equivalent of the compound of general formula (VI) is used and preferably again the compound of general formula (VI) is added to a preformed mixture of hydroquinone and the base. Suitably the compound of general formula VI is used or stored in association with a polymerisation inhibitor. After the reaction, the reaction mixture can be poured into water, and the mixture so obtained concentrated and extracted with a suitable solvent. After evaporation of the solvent, the residue so obtained can be purified by distillation.

The reaction of the compound of general formula (III) with the compound of general formula (IV) to give the compound of general formula (II) is suitably performed in the presence of a dry base and a solvent or diluent. Examples of suitable solvents are lower alkyl ketones, for example methyl ethyl ketone. The reaction may be accelerated by heating and may for example be conveniently carried out at the reflux temperature of the solvent. Examples of suitable bases are inorganic bases such as sodium or potassium carbonate. If desired, a mixture of a compound of general formula (IV) wherein X is chlorine with a compound wherein X is fluorine can be used.

Suitable ways of carrying out the reduction step can be found for example in Harrison and Harrison, Compendium of Organic Synthetic Methods, 1971, Volume I, pages 198 to 202, published by Wiley Interscience), the disclosure of which document is incorporated herein by reference. One way is to hydrogenate the compound of general formula (II) in the presence of a palladium or platinum catalyst and a suitable solvent. After the hydrogenation, the catalyst can be filtered off and the solvent removed to give the product as an oil which can be purified by chromatography, distillation or crystallisation.

As indicated above, the group $R^1$ in the compounds of general formula (I), (II) and (III) can be converted to another group $R^1$. For example, the compounds wherein $R^1$ is an ester group can be hydrolysed to the corresponding acid and then the amides, salts and other esters can be prepared from the acid by methods known in the art. Alternatively, transesterification techniques can be used to prepare other esters.

The compounds of general formula (II) and (III) are novel compounds, and as such form part of the present invention.

Hydroquinone and the compounds of general formula (IV) and (VI) are old compounds; they can be prepared by methods known in the art. The compounds of general formula (V) and details of their preparation are disclosed in European Patent Application No. 78300203.3.

The compounds of general formula (I) contain a chiral centre. One of the enantiomers is believed to be a more active herbicide than the other enantiomer. For example, in the case of the compounds of general formula (I) wherein Z is trifluoromethyl and Y is hydrogen, the D(+)enantiomer is more active than the corresponding L(−)enantiomer. Our European Patent Application No. 79300234.6 (Publication No. 0003890; the disclosure of this Application is incorporated herein by reference) discloses more details of the enantiomers.

Such enantiomers can be obtained in the substantially pure state by resolution of the racemic mixture of the compound of general formula (I) or alternatively the reduction stage can be performed in the presence of a suitable chiral catalyst in order to produce the desired enantiomer direct. Suitable chiral catalysts are for example the Wilkinson's catalysts rhodium [1,2-bis(O-anisylphenylphosphino)ethane] or a rhodium-chiral-O-anisylcyclohexylmethylphosphine complex.

The compounds of general formula (II) have herbicidal activity; they are in general more effective against grass species than against broad-leafed species of plants.

The invention is illustrated by the following Examples; the temperatures are given in degrees Centigrade (°C.).

EXAMPLE 1

Step 1

To n-butyl acrylate (100 g, 0.78 mole) and carbon tetrachloride (260 ml) was slowly added bromine (125 g, 0.78 mole). Initially the reaction mixture was warmed to 50° to start the reaction and was then maintained at 50°–60° until most of the bromine had been added. The mixture was then heated at 70° for a short time. The crude reaction mixture was evaporated under reduced pressure to remove volatile material, redissolved in dichloromethane, washed with brine, dried (Na$_2$SO$_4$) and distilled to obtain n-butyl 2,3-dibromopropionate (174 g; 77%), bp 75°–80°/0.3 mmHg.

Step 2 n-Butyl 2,3-dibromopropionate (144 g, 0.5 mole) containing p-methoxyphenol (0.5 g) was stirred vigorously under nitrogen and at room temperature, whilst 20% w/v aqueous caustic potash solution was slowly added. The course of the dehydrobromination was constantly monitored by gas-liquid chromatography. From time to time the reaction mixture was allowed to separate and the almost neutral aqueous phase discarded, in order to maintain that effective concentration of the added base. When more than 95% of the starting material had been consumed, the reaction was stopped and the lower organic layer run off and washed with water. After drying (Na$_2$SO$_4$), the crude product was distilled to give a main fraction which was n-butyl 2-bromoacrylate (yield 72%), bp 92°/17 mmHg.

Step 3

To a 1 liter flask fitted with a stirrer, thermometer, condenser and nitrogen inlet were charged 4-(trifluoromethylpyrid-2-yloxy)phenol (38.4 g, 0.15 mole), n-butyl 2-bromoacrylate (31.2 g, 0.15 mole), anhydrous potassium carbonate (120 g, 0.87 mole) and dry acetonitrile (500 mls). The mixture was stirred vigorously under reflux and under a nitrogen atmosphere for 16 hours. The mixture was then cooled, filtered and the filtrate evaporated under reduced pressure. The crude product was redissolved in dichloromethane, cooled, filtered again, dried (Na$_2$SO$_4$), re-evaporated and subjected to short-path distillation at 160°–170°/0.2 mmHg to give n-butyl 2-[4-(5-trifluoromethylpyrid-2-yloxy)-phenoxy]acrylate (43.2 g).

Step 4

The product (15 g) from Step 3 in n-butanol (300 ml) was hydrogenated at room temperature and atmospheric pressure using a 10% palladium on carbon catalyst. When the uptake of hydrogen ceased, the catalyst was filtered off and the filtrate evaporated under reduced pressure. The residue was purified by short-path distillation (at 140°–150°/0.2 mmHg) to afford a main fraction (11.6 g) containing 57% w/w of the desired propionate which was recrystallised from cold hexane to give n-butyl 2-[4-(5-trifluoromethylpyrid-2-yloxy)-phenoxy]propionate. The propionate may then be obtained substantially pure by recrystallisation from cold hexane.

EXAMPLE 2

Step 1

To n-butyl acrylate (300 g) and carbon tetrachloride (780 ml) stirred at 50° was added bromine (375 g) dropwise over 5 hours. During the course of the addition the temperature was gradually raised to 70°. The reaction mixture was allowed to cool and left at room temperature for a further 16 hours, after which it was distilled to give n-butyl 2,3-dibromo-propionate (650 g; 96%), bp 72°/0.1 mmHg.

Step 2

The product (300 g) of Step 1 and p-methoxyphenol (2 g) was added to a 2 l. round bottom flask fitted with a thermometer, condenser, stirrer and inlet for nitrogen, and containing acetonitrile (1000 ml) and anhydrous potassium carbonate (330 g). The reaction mixture was stirred under reflux for 8 hours and cooled, and the salts were filtered off. The filtrate was evaporated under reduced pressure to remove the solvent, and the residue was dissolved in dichloromethane. The solution was dried (Na$_2$SO$_4$), filtered and evaporated. Distillation of the residue afforded n-butyl 2-bromoacrylate (196 g; 90%), b.p. 90°/15 mmHg.

Step 3

Sodium (6.9 g, 0.3 mol) was added to n-butanol (200 ml) under nitrogen. When the sodium had reacted, the solution was cooled to room temperature and hydroquinone (16.5 g, 0.15 mol) was added. The temperature was raised to 45° and n-butyl 2-bromoacrylate (26 g, 0.125 mol) was added dropwise. When the acrylate had all been added, the mixture was stirred for 20 hours and then 2-chloro-5-trifluoromethylpyridine (27.2 g, 0.15 mol) was added. The resulting mixture was heated for 30 hours at 65°, allowed to cool, treated with carbon and filtered through Celite. The resulting solution was made up to 500 ml with n-butanol and a hydrogenation catalyst (10% palladium on carbon; 0.5 g) was added. The crude product was hydrogenated at ambient temperature and pressure until hydrogen uptake ceased to give n-butyl 2-[4-(5-trifluoromethylpyridin-2-yloxy)-phenoxy]propionate.

We claim:

1. A process for preparing a compound of general formula (I):

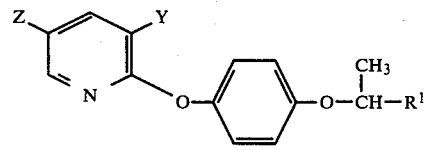

wherein Z is trifluoromethyl or difluoromethyl, Y is hydrogen or chlorine; and R$^1$ is optionally halo-, alkoxy- or hydroxy substituted alkoxycarbonyl of to 8 carbons; optionally halo- or methyl-substituted cyclohexyloxycarbonyl; (C$_{3-6}$ alkenyl) oxycarbonyl; optionally halo- or methyl-substituted phenoxycarbonyl; or benzyloxycarbonyl, the phenyl moiety of which is optionally ring-substituted with halogen or methyl; or, in the case of a said compound wherein $R^1$ is carboxyl, alkali metal, alkaline earth metal or ammonium salt thereof; said process consisting essentially of the step of selectivity reducing a compound of general formula (II):

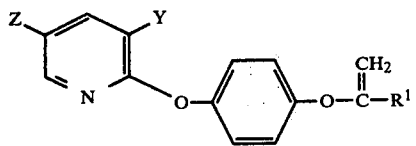

wherein Z, Y and $R^1$ are as defined above, and if necessary, when $R^1$ in said compound of general formula (I) so obtained is carboxy, esterifying the compound to give a compound of general formula (I) wherein $R^1$ is as defined above other than carboxy or alkali metal, alkaline earth metal or ammonium salt thereof, or when $R^1$ in said compound of general formula (I) so obtained is as defined above other than carboxy, hydrolysing the compound to give a compound of general formula (I) wherein $R^1$ is carboxy or alkali metal, alkaline earth metal or ammonium salt thereof, said reduction involving hydrogenation of said compound (II) in the presence of a palladium or platinum catalyst, the reduction being performed until the alkene double bond is saturated after which the catalyst is removed and the product obtained corresponding to compound (I) is purified.

* * * * *